United States Patent [19]

Yavitz et al.

[11] Patent Number: 5,538,301
[45] Date of Patent: Jul. 23, 1996

[54] CONTACT LENS APPLICATOR

[76] Inventors: Edward Q. Yavitz, 3828 Spring Creek Rd., Rockford, Ill. 61114; Randall S. Yavitz, 37 W. Morten Ave., Phoeniz, Ariz. 85021

[21] Appl. No.: 467,740

[22] Filed: Jun. 6, 1995

[51] Int. Cl.[6] .................................................. A61F 9/00
[52] U.S. Cl. ................................. 294/1.2; 206/5.1
[58] Field of Search ............... 294/1.2, 25; 15/214; 134/901; 206/5.1

[56] References Cited

U.S. PATENT DOCUMENTS

| | | | |
|---|---|---|---|
| 3,091,328 | 5/1963 | Leonardos | 294/1.2 |
| 3,584,908 | 6/1971 | Ray | 294/1.2 |
| 3,647,380 | 3/1972 | Middleton | 294/1.2 X |
| 4,232,966 | 11/1980 | Schpak et al. | 294/1.2 X |
| 4,545,478 | 10/1985 | Waldman | 294/1.2 X |
| 4,750,771 | 6/1988 | Emmett et al. | 294/1.2 X |
| 4,753,470 | 6/1988 | Menard | 294/1.2 |
| 5,071,276 | 12/1991 | Nielsen et al. | 206/5.1 X |
| 5,348,358 | 9/1994 | Selick | 294/1.2 |

FOREIGN PATENT DOCUMENTS 3822654   1/1990   Germany ................... 294/1.2

*Primary Examiner*—Johnny D. Cherry
*Attorney, Agent, or Firm*—Foley & Lardner

[57] ABSTRACT

A contact lens device is disclosed. The device is designed to facilitate the application of a contact lens, particularly an extended wear type contact lens, onto an eye of a wearer. The device includes an applicator preferably made of a conformable material. The applicator has a contoured surface designed to substantially engage and hold the contact lens while the wearer moves the contact lens into proximity with one of his eyes. The applicator is also sufficiently deformable to permit the contact lens to be pressed into substantial contact with the wearer's eye where the superior adhesion between the corneal surface of the eye and the contact lens removes the lens from the applicator when the applicator is pulled away by the wearer.

22 Claims, 1 Drawing Sheet

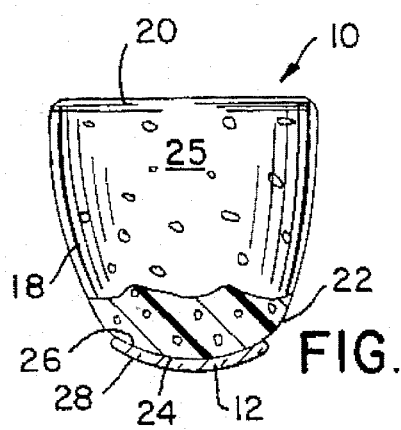
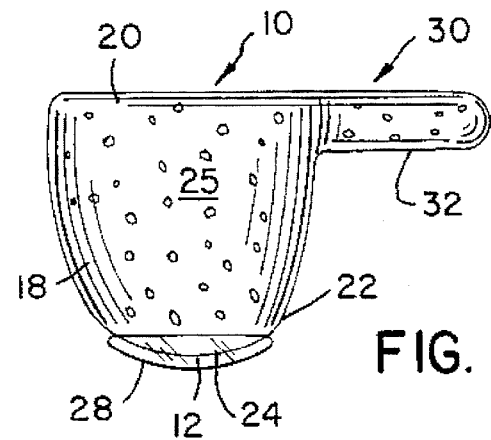
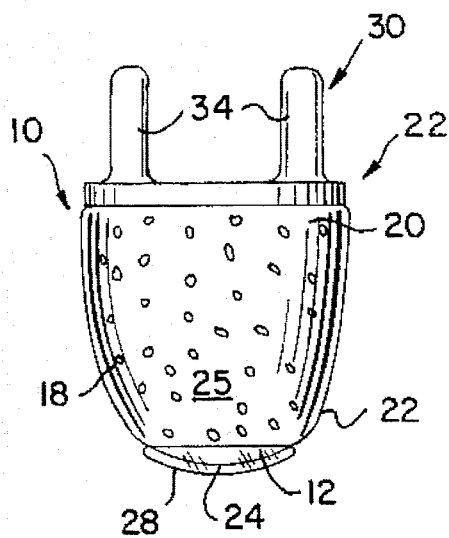
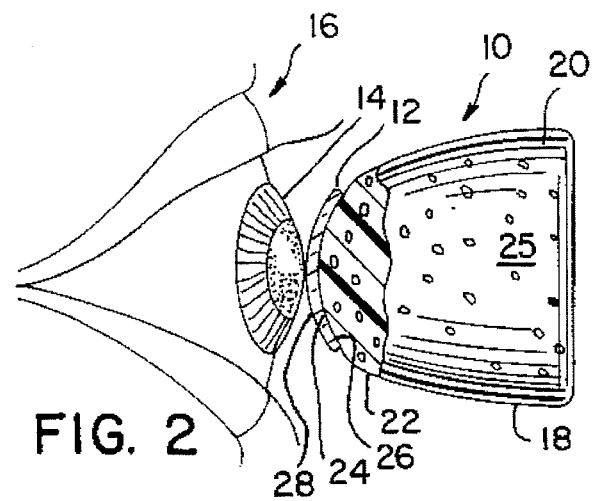
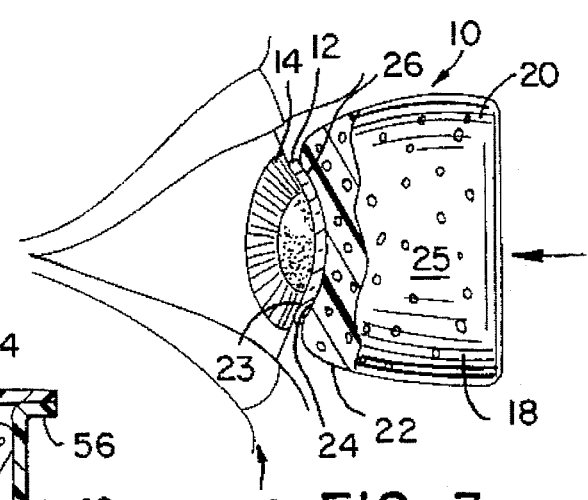
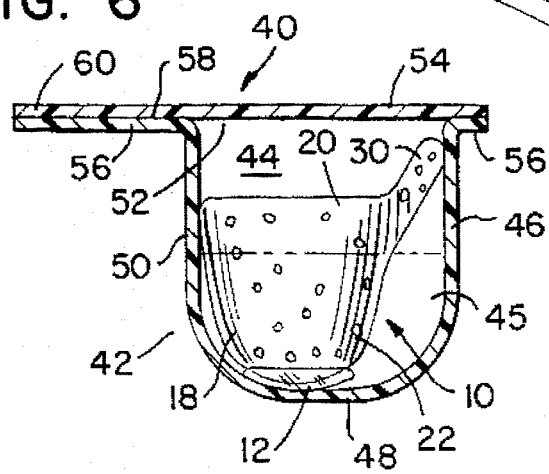

CONTACT LENS APPLICATOR

FIELD OF THE INVENTION

The present invention relates generally to a device and system for applying a contact lens to the eye of a wearer, and particularly to a deformable applicator designed to hold a contact lens and transfer the contact lens to the eye.

BACKGROUND OF THE INVENTION

For many years, contact lenses have been used to correct a variety of vision problems. Some contact lenses are made of a hard inflexible plastic or glass, and others are made of a softer flexible plastic formed in a thin, circular sheet. Each contact lens has a natural curvature that substantially matches the curvature of the eye to permit adherence of the contact to the surface of the eye. However, the exact curvature of the contact lens relative to the curvature of the wearer's eye must be determined according to the wearer's particular vision problem.

Some soft contact lenses, known as "extended wear" contact lenses, have become increasingly popular. These contact lenses are typically made of a relatively thin and flexible plastic material and are designed to remain on the eye of a wearer for extended periods of time, such as multiple days or more. After passage of the appropriate period of time, the wearer simply removes the contact lens, disposes of it and replaces it with a new extended wear contact lens. The extended wearability reduces the time required for insertion and removal of contact lenses, normally done on a daily basis.

Companies manufacturing extended wear contact lenses have reduced the material costs and increased the comfort of the contact lenses by making them thinner than conventional hard or soft contact lenses. However, the reduced thickness of the contact lens causes difficulty in applying the contact lens to the surface of the wearer's eye.

Normally, the extended wear, disposable contact lens is packaged in a saline solution, and the wearer simply grasps the lens and applies it to an eye with his or her finger. For example, the contact lens may be grasped between the thumb and forefinger and then pressed onto the eye with the forefinger. With thinner contact lenses, there is a greater tendency for the lens to fold on itself or invert and wrap about the tip of the forefinger. It then becomes difficult to achieve transference of the contact lens from the finger to the eye, because the contact lens tends to stick to the wearer's finger rather than his eye. This results in inadvertent removal or dislodging of the lens as the wearer's finger is pulled away from the eye.

Dirt and bacteria inherently carried on finger tips can also be problematic, because they are moved with the contact lens directly into fluid contact with the eye. It would be advantageous to provide a contact lens applicator designed to conform to the surface shape of the wearer's eye and to release the contact lens onto the eye without contamination from dirt or bacteria.

SUMMARY OF THE INVENTION

The present invention features a contact lens device designed to facilitate the application of a contact lens onto the eye of a wearer. The device includes an applicator made of a conformable material and having an exterior surface configured to engage the outer curvature of the contact lens. The conformable material is sufficiently flexible to permit the pressing of the contact lens onto the eye of the wearer. Preferably, the conformable material is hydrophilic and has a contoured surface designed to substantially contact and hold the outer surface of the contact lens when the contact lens is adjacent the applicator. However, the conformable material is sufficiently flexible to permit transition of the contoured surface to a generally concave shape as the contact lens is pressed onto the eye.

According to another aspect of the invention, a contact lens applicator system is provided. The system includes a container package having a cavity and a liquid disposed within the cavity. A contact lens is also disposed within the cavity, and a flexible contact lens applicator is maintained adjacent the container package, preferably within the cavity.

BRIEF DESCRIPTION OF THE DRAWINGS

The invention will hereafter be described with reference to the accompanying drawings, wherein like reference numerals denote like elements, and:

FIG. 1 is a front view of an applicator designed according to a preferred embodiment of the invention and including a partial cut-away portion showing a contact lens adjoined thereto;

FIG. 2 illustrates use of the applicator of FIG. 1 to move a contact lens into proximity with the eye of a wearer;

FIG. 3 illustrates the contact lens being pressed onto the surface of the wearer's eye via the applicator illustrated in FIG. 1;

FIG. 4 is a front view of an alternate embodiment of the invention illustrated in FIG. 1;

FIG. 5 is a front view of another alternate embodiment of the invention illustrated in FIG. 1; and FIG. 6 is a cross-sectional view of an overall contact lens applicator system designed according to a preferred embodiment of the invention and showing an applicator adjoined to a container.

DETAILED DESCRIPTION OF THE PREFERRED EMBODIMENT

Referring generally to FIGS. 1–3, a contact lens device 10 according to a preferred embodiment of the invention is illustrated. Contact lens device 10 is designed to facilitate the application of a contact lens 12 onto an eye 14 of a wearer 16. Contact lens device 10 includes an applicator 18 having a base end 20 and a lens holding end 22 which includes a contoured surface 24.

Lens holding end 22, and preferably applicator 18, are made of a material 25 that is preferably conformable and hydrophilic, designed to receive a liquid, such as saline solution. A variety of such materials may be available, although foam rubber has been determined to work well by both receiving and absorbing liquid. This facilitates the proper hydration of contact lens 12 and the adhering of contact lens 12 to contoured surface 24 when they are placed into contact with each other. Foam rubber and other porous materials are able to absorb liquid which helps the transfer of contact lens 12 to eye 14, but other materials will also work if the adhesion between the material and contact lens 12 is less than the adhesion between eye 14 and contact lens 12 when the lens is pressed into cooperation with the eye. For example, materials such as low density polyethylene, teflon foam or polystyrene could potentially be used alone or in combination with an appropriate fluid.

Contact lens 12 has an outer surface 26, that is contacted by contoured surface 24, and an inner surface 28, generally opposite outer surface 26 and designed to cooperate with the surface of eye 14. Lens holding end 22 and its contoured surface 24 should be sufficiently deformable to permit conformation of contoured surface 24 to eye 14 when lens 12 is pressed onto eye 14 of wearer 16. Contoured surface 24 can be made in a variety of configurations, including generally concave configurations. With those configurations, outer surface 26 of contact lens 12 remains substantially in its natural state of curvature, and lens 12 may be applied to eye 14 with very little deformation of contoured surface 24. However, in the illustrated embodiment, contoured surface 24 is generally convex and may, for instance, be substantially hemispherical in shape. Thus, when applicator 18 is pressed against outer surface 26, contact lens 12 is inverted or flexed until the curvature of contact lens 12 is generally opposite the curvature of eye 14 as illustrated in FIG. 2. Then, as contact lens 12 is gently pressed into cooperation with eye 14, contoured surface 24 and lens holding end 22 deform to flex contact lens 12 towards eye 14 until its curvature returns to generally match the curvature of eye 14 as illustrated in FIG. 3. The reader should note that when applied to eye 14, contact lens 12 may have a somewhat different curvature than the curvature of the surface of eye 14 to achieve the desired optical effects.

To apply contact lens 12 to eye 14, contoured surface 24 of applicator 18 is preferably first wetted with a liquid, such as saline solution, and then pressed against outer surface 26 of contact lens 12. Lens holding end 22 may comprise a material that will absorb a small amount of the liquid. The wetted contoured surface 24 sufficiently adheres to the generally smooth outer surface 26 of contact lens 12 to permit the wearer to grip base end 20 and lift applicator 18 and contact lens 12 towards eye 14. Applicator 18 and contact lens 12 are then moved into proximity with eye 14 as illustrated in FIG. 2. Wearer 16 continues to gently press contact lens 12 towards eye 14 until contact lens inner surface 28 sufficiently engages the surface of eye 14. At this point, the adhesion between eye 14 and inner surface 28 is greater than the adhesion between contoured surface 24 and outer surface 26. This allows applicator 18 to be moved away from eye 14 without disturbing the position of contact lens 12 on eye 14. Thus, a variety of materials, often in combination with a fluid such as saline solution, could be used to move contact lens 12 to eye 14, provided the adhesion between contoured surface 24 and contact lens 12 is sufficient to lift contact lens 12 to eye 14 but not so great as to prevent or inhibit the transfer of contact lens 12 to eye 14 when placed in contact therewith.

Alternate embodiments of contact lens device 10 are illustrated in FIGS. 4 and 5, but reference numerals have been kept consistent with those of FIGS. 1–3 where possible. In each of these figures, a handle 30 is illustrated as attached to applicator 18. In the embodiment illustrated in FIG. 4, handle 30 preferably comprises the same or similar material as that of applicator 18 and includes a tab 32 extending generally radially outward from base end 20. In the embodiment illustrated in FIG. 5, handle 30 preferably includes a pair of prongs 34 extending from base end 20 in a generally axial direction. It should be noted that a variety of handles 30 could be used to facilitate the gripping of applicator 18, and the handles illustrated in FIGS. 4 and 5 are only two examples of many that would be understood by one of ordinary skill in the art to facilitate the gripping and handling of applicator 18.

Referring generally to FIG. 6, a contact lens applicator system 40, according to a preferred aspect of the invention, is illustrated. Contact lens applicator system 40 includes a container package 42 having a cavity 44. A liquid 45, such as a saline solution, is disposed within cavity 44, and at least partially fills cavity 44. Cavity 44 is defined by an outer wall 46 comprising a bottom 48 and at least one side wall 50 extending from bottom 48 to form a top opening 52. Preferably, top opening 52 is sealed by a cover or membrane 54. Side wall 50 may terminate opposite bottom 48 with an outwardly extending flange 56 to which membrane 54 is sealingly adhered by, for instance, an adhesive 58. Membrane 54 may also have a flap portion 60 to facilitate the peeling away of membrane 54 to expose cavity 44.

Contact lens 12 is disposed within cavity 44, and any of the contact lens devices 10 described above may be adjoined to container package 42. The desired contact lens device 10 may be attached to the outside of container package 42; it may be disposed within a separate cavity (not shown) of container package 42, or it may be combined with container package 42 in any other of a variety of ways as would be understood by one of ordinary skill in the art. In the illustrated embodiment, contact lens device 10 is disposed within cavity 44, and preferably disposed in contact with liquid 45 and outer surface 26 of contact lens 12.

As illustrated, device 10 is located so contoured surface 24 engages outer surface 26 of contact lens 12. Thus, to use applicator system 40, wearer 16 simply grasps cover 54 by, for instance, flap portion 60 and peels it away from outer wall 46 to expose cavity 44. Wearer 16 may then grasp applicator 18 and remove it and the adjoined contact lens 12 from cavity 45. Applicator 18 and contact lens 12 are placed in proximity to eye 14 as illustrated in FIG. 2. The wearer may then gently press contact lens 12 against eye 14 with applicator 18, until applicator 18 deforms sufficiently to flex the inner surface 28 of contact lens 12 into substantial conformity with the surface of eye 14. Contact lens device 10 is then moved away from eye 14 leaving the contact lens securely in place on eye 14.

It will be understood that the foregoing description is of a preferred exemplary embodiment of this invention and that the invention is not limited to the specific forms shown. For example, the applicator may be made from a variety of materials, the contoured surface may have various contours, the base and handle, if any, may be formed in numerous shapes and orientations, the container package may have one or more cavities and may be made in multiple configurations. These and other modifications may be made in the design and the arrangement of the elements without departing from the scope of the invention as expressed in the appended claims.

What is claimed is:

1. A contact lens device for facilitating the application of a contact lens onto an eye of a wearer, the contact lens having an inner surface designed to contact the eye and an outer surface, comprising:

a liquid pervious applicator including a conformable material having a generally convex surface configured to substantially engage the outer surface of the contact lens, the conformable material being sufficiently deformable to permit transition of the generally convex surface to a generally concave surface as the applicator presses the contact lens onto the eye; and a liquid applied to the conformable material to facilitate engagement of the outer surface.

2. The contact lens device as recited in claim 1, wherein the conformable material comprises a porous material.

3. The contact lens device as recited in claim 2, wherein the porous material is a liquid absorbent foam rubber.

4. The contact lens device as recited in claim 1, further comprising a handle attached to the applicator and configured for gripping by the wearer.

5. The contact lens device as recited in claim 1, wherein the conformable material is generally hemispherical when in its natural shape.

6. A contact lens applicator system, comprising:

a disposable container having a cavity;

a liquid disposed within the cavity;

a soft contact lens disposed within the cavity;

a conformable contact lens applicator adjoined to the container, the conformable contact lens applicator including a liquid retaining surface that adheres the soft contact lens when wetted with the liquid; and a peelable cover attached to the disposable container over the cavity to permit opening of the cavity by peeling away the cover.

7. The contact lens applicator system as recited in claim 6, wherein the conformable contact lens applicator includes a porous material having a curved surface configured to engage a contact lens.

8. The contact lens applicator system as recited in claim 7, wherein the curved surface is generally convex, the porous material being sufficiently deformable to permit transition of the curved surface from generally convex to generally concave as the contact lens and applicator are pressed into engagement with an eye of a wearer.

9. The contact lens applicator system as recited in claim 7, wherein the liquid comprises a saline solution.

10. The contact lens applicator system as recited in claim 9, wherein the container includes an outer wall in which the cavity is formed and a cover layer attached to the outer wall over the cavity to seal the liquid therein.

11. The contact lens applicator system as recited in claim 9, wherein the conformable contact lens applicator is disposed within the cavity.

12. The contact lens applicator system as recited in claim 6, wherein the conformable contact lens applicator is liquid absorbent.

13. The contact lens applicator system as recited in claim 12, wherein the conformable contact lens applicator further includes a handle to facilitate gripping thereof.

14. The contact lens applicator system as recited in claim 6, wherein the conformable contact lens applicator is porous.

15. A contact lens device for facilitating the application of a contact lens onto an eye of a wearer, the contact lens being of the type having an outer surface and an inner surface configured to contact the eye, comprising:

an applicator having a base end and a lens holding end, the lens holding end including a contoured surface designed to engage the outer surface over a sufficiently large area to hold the contact lens when the contoured surface is wetted, wherein the contoured surface is deformable to permit conformation to the eye when the contact lens is pressed onto the eye of the wearer, wherein the contoured surface is sufficiently porous to absorb liquid.

16. The contact lens device as recited in claim 15, wherein the lens holding end comprises foam rubber.

17. The contact lens device as recited in claim 15, wherein the contoured surface is convex.

18. A method of forming and using an applicator for applying a contact lens to the surface of an eye, comprising the steps of:

forming an applicator of a single material that has a flexible, hydrophilic surface;

contouring the flexible, hydrophilic surface to substantially engage an outer surface of the contact lens;

wetting the flexible hydrophilic surface with a liquid;

placing the flexible, hydrophilic surface into contact with the outer surface;

adhering the contact lens to the applicator via the liquid;

moving the applicator and contact lens into proximity with the eye;

pressing the applicator towards the eye until the applicator sufficiently deforms to move the contact lens into engagement with the eye.

19. The method as recited in claim 18, wherein the step of contouring includes contouring the flexible, hydrophilic surface into a generally convex shape.

20. A contact lens device for facilitating the application of a contact lens onto an eye of a wearer, the contact lens being of the type having an outer surface and an inner surface configured to contact the eye, comprising:

an applicator having a contoured surface designed to contact the outer surface of the contact lens, the contoured surface including a material that, when wetted and moved into contact with the outer surface, creates an attractive force, wherein the attractive force is less than the adhesive force created between the corneal surface of the eye and the contact lens when the contact lens is moved into engagement with the eye;

a case having a cavity designed to receive the applicator and a liquid; and a peel off cover that can be peeled away to expose the cavity.

21. The contact lens device as recited in claim 20, wherein the contoured surface is deformable.

22. The contact lens device as recited in claim 21, wherein the contoured surface is porous.

* * * * *